(12) United States Patent
Burrell

(10) Patent No.: US 6,489,539 B1
(45) Date of Patent: Dec. 3, 2002

(54) METHOD FOR ALTERING CARBOHYDRATE METABOLITE LEVELS IN STORED POTATO TUBERS

(75) Inventor: Michael Meyrick Burrell, Cambridge (GB)

(73) Assignee: Advanced Technologies (Cambridge), Limited, Cambridge (GB)

( * ) Notice: Subject to any disclaimer, the term of this patent is extended or adjusted under 35 U.S.C. 154(b) by 195 days.

(21) Appl. No.: 09/115,356

(22) Filed: Jul. 14, 1998

Related U.S. Application Data

(62) Division of application No. 08/284,199, filed on Aug. 2, 1994, which is a continuation of application No. 07/991,451, filed on Dec. 16, 1992, now Pat. No. 5,387,756, which is a continuation of application No. 07/628,216, filed on Dec. 17, 1990, now abandoned.

(30) Foreign Application Priority Data

Dec. 21, 1989 (GB) .............................. 8928937
Jul. 6, 1990 (GB) .............................. 9014988

(51) Int. Cl.[7] ........................ C12N 15/82; C12N 15/31; C12P 19/04; A01H 5/00; A01H 5/06
(52) U.S. Cl. ...................... 800/284; 800/278; 800/287; 800/288; 800/317.2; 47/58.1; 435/101; 435/194
(58) Field of Search .............................. 435/69.1, 70.1, 435/100, 101, 194, 468; 800/284, 287, 298, 317.2; 47/58.1; 88/288

(56) References Cited

U.S. PATENT DOCUMENTS

| | | | |
|---|---|---|---|
| 4,801,540 A | 1/1989 | Hiatt et al. | 435/172.3 |
| 4,940,835 A | 7/1990 | Shah et al. | 800/205 |
| 4,971,908 A | 11/1990 | Kishore et al. | 435/172.1 |
| 5,387,756 A | 2/1995 | Burrell et al. | 800/205 |
| 5,648,249 A | 7/1997 | Barry et al. | 435/172.3 |

FOREIGN PATENT DOCUMENTS

| | | |
|---|---|---|
| EP | 0 368 506 A2 | 10/1989 |
| WO | WO 88/09334 | 12/1988 |
| WO | WO 89/08145 | 9/1989 |
| WO | WO 94/24292 | 10/1994 |

OTHER PUBLICATIONS

Olive, 1988, Ph.D. Thesis, University of Warwick.
Anderson et al., 1989, *J. Biol. Chem.* 264:12238–12242.
Anderson et al., 1990, Vayda & Park (eds) *The Molecular Biology of the Potato*, C.A.B. International, Wallingford, pp. 159–180.
Anderson et al., 1991, *Gene* 97:199–205.
Anderson et al., 1995, *Plant Physiol.* 108(2 Suppl.):30.
T. ap Rees, 1988, *Biochemistry of Plants: A Comprehensive Treatise* 14:1–33.
ap Rees et al., 1988, *Symp. Soc. Exp. Biol.* 42:377–393.

Baecker et al., 1982, *Miami Winter Symposia* 19:509.
Baecker et al., 1983, *Ann. Meet. Am. Soc. Microbiol. Abstr.* p. 106.
Baecker et al., 1983, *FASEB* 42:1968.
Baecker et al., 1983, *J. Biol. Chem.* 258:5084–5088.
Bae et al., 1990, *Maydica* 35:317–322.
Ball et al., 1991, *Planta* 185:17–26.
Ball and Preiss, 1994, *J. Biol. Chem.* 269:24706–24711.
Bloom et al., 1987, *Fed. Proc.* 46:2055.
Brangeon et al., 1997, *Plant Physiol. Biochem.* 35:847–858.
Burrell et al., 1993, British Crop Protection Council Monograph, No. 55, Opportunities for Molecular Biology in Crop Production; *Int'l Symp.*, Cambridge, England, pp. 197–201.
M. Burrell, 1993, Biotechnology in Agriculture, No. 12. The molecular and cellular biology of the protato, 2nd ed.; 34 *Int'l Symp.*, Santa Cruz, CA, pp. 45–55.
Burrell et al., 1994, *J. Cellular Biochem. Suppl.* 0(18 Part A):119.
Cervantes et al., 1989, *Physiol. Plant* 77:52–58.
B. Chen, 1995, *Diss. Absts. Intl.* 57:932–B.
Colosia et al., 1989, *Diss. Abstr. Tnt.* 50:854–B.
Copeland et al., 1981, *Plant Physiol.* 68:996–1001.
H. Davies, 1996, *Potato Research* 39:411–427.
Denyer et al., 1996, *Plant Physiol.* 112:779–785.
Dickinson et al., 1969, *Planta Physiol.* 44:1058–1062.
Duffus et al., 1984, *Regulation of Carbohydrate Metabolism In: Carbohydrate Metabolism in Plants* Longman: London & New York, pp. 145–154.
du Jardin et al., 1991, *Plant Mol. Gen.* pp. 349–351.
Elson et al., 1990, *Genomics* 71:47–56.
Fromm et al., 1993, *Phil Trans. R. Soc. Lond. B* 339:223–237.
Fu et al., 1996, *FASEB J.* 10:A1384.
Geigenberger et al., 1997, *Planta* 201:502–518.
Ghosh and Preiss, 1965, *Biochem.* 4:1354–1361.
Ghosh and Preiss, 1966, *J. Biol. Chem.* 241:4491–4504.
Giroux et al., 1994, *Mol. Gen. Genet.* 243:400–408.
Giroux et al., 1996, *Proc. Natl. Acad. Sci.* 93:5824–5829.
Greene et al., 1994, *Plant Physiol.* 105 (1 Suppl.):46.
Greene et al., 1996, *PNAS* 93:1509–1513.
Hawker et al., 1979, *Physiol. Plant* 46:25–30.
Jeannette et al., 1994, *Plant & Cell Physiol.* 35:869–878.
Kim et al., 1989, *Plant Physiol.* 91:217–220.
Klosgen et al., 1986, *Mol. Gen. Genet.* 203:237–244.
Krishnan et al., 1986, *Plant Physiol.* 81:642–645.
Kumar et al., 1989, *J. Biol. Chem.* 264:10464–10471.
Laughlin et al., 1996, *FASEB J.* 10:A1502.

(List continued on next page.)

Primary Examiner—David T. Fox
(74) Attorney, Agent, or Firm—Pennie & Edmonds LLP

(57) ABSTRACT

Transgenic potato plants are prepared by a method which transforms potato plants with a chimeric gene comprising a promoter and sequence encoding a phosphofructose kinase, which regulates the amount of a metabolite in a pathway for the synthesis or degradation of starch, sucrose or reducing sugar. In stored transgenic potato tubers of the invention an increased level of phosphofructose kinase results in reduced accumulation of sugars.

2 Claims, 3 Drawing Sheets

OTHER PUBLICATIONS

Lee et al., 1985, *FASEB Proc.* 44:1418.
Lee et al., 1987, *Nuc. Acids Res.* 15:10603.
Leung et al., 1986, *Ann. Meet. Am. Soc. Microbiol. Abstr.* p. 127.
Leung et al., 1986, *J. Bacteriol.* 167:82–88.
Leung et al., 1987, *Diss. Abstr. Int.* 47:4767–B.
Leung et al., 1987, *J. Bacteriol.* 169:4349–4354.
Leung et al., 1987, *J. Bacteriol.* 169:4355–4360.
Li et al., 1992, *Carbohydr. Res.* 227:227–239.
Lin et al., 1988, *Plant Physiol.* 86:1131–1135.
Lin et al., 1988, *Plant Physiol.* 88:1175–1181.
Meyer et al., 1993, *Arch. Bicho. Biophys.* 302:64–71.
Miller et al., 1995, *Planta* 197:522–527.
Mitten et al., 1991, *The Molecular and Cellular Biology of the Potato*, pp. 181–191.
Morell et al., 1987, *Plant Gene Systems and Thier Systems*, Proceedings of a CIBA–GEIGY–UCLA Symposium, Tamarron, Colorado, USA 62:227–242.
B. Muller–Rober, 1990, *Mol. Gen. Genet.* 224:136–146.
Nakata et al., 1991, *Plant Molec. Biol.* 17:1089–1093.
Nakata et al., 1994, *J. Biol. Chem.* 269:30798–30807.
T. Okita, 1992, *Plant Physiol.* 100:560–564.
Olive et al., 1989, *Plant Mol. Biol.* 12:525–538.
Peloewetse et al., 1995, *J. Exper. Botany* 46(Suppl.):10.
J. Preiss, 1969, XI Int'l Botanical Congress. Abstracts of the Papers Presented at the XI Intl. Botanical Congress and the Intl. Wood Chemistry Symposium 206p; Seattle, WA, p. 173.
J. Preiss, 1981, *XIII Int. Bot. Congress* 13:315.
J. Preiss, 1982, *Ann. Rev. Plant Physiol.* 33:431–454.
J. Preiss, 1984, *Ann. Rev. Microbiol.* 38:419–458.
J. Preiss, 1988, *The Biochemistry of Plants*, Ed. by J. Preiss, Orlando, FL: Academic Press. pp. 184–249.
J. Preiss, 1991, *Oxford Surveys of Plant Molec. & Cell Biol.* 7:59–114.
J. Preiss, 1996, *Cereal Foods World* 41:587–588.
Preiss and Kosuge, 1976, Bonner & Varner (eds.); *Plant Biochemistry* 3rd Ed., Academic Press:New York, NY, pp. 277–336.
Preiss and Levi, 1980, *The Biochem. of Plants*, pp. 371–423.
Preiss and Walsh, Chapter 5, "The comparative biochemistry of glycogen and starch", pp. 200–315.
Preiss et al., 1967, *Biochemistry of Chloroplasts* 2:131–153.
Preiss et al., 1973, *ANYAS* 210:265–278.
Preiss et al., 1984, 188th American Chemical Society Meeting, Philadelphia, PA, *Abstr. Pap. Am. Chem. Soc.* p. 188.
Preiss et al., 1987, *J. Cell Biochem. Suppl. 0* (11 Part B):11.
Preiss et al., 1988, Third Chemical Congress of North America HelD at the 195th American Chemical Society meeting, Toronto, Ontario, Canada, *Abstr. Pap. Chem. Congr. North AM* 3:21.
Preiss et al., 1989, *Adv. Microbial Physiol.* 30:183–238.
Preiss et al., 1993, Improvement of Cereal Quality by Genetic Engineering (Henry, R.J. & J.A. Ronalds, eds.); Guthrie Centenary Conference of the Royal Australian Chemical Institute Cereal Chemistry Division, Sydney, New South Wales, Australia, pp. 115–127.
Robinson et al., 1988, *Plant Physiol.* 87:727–730.
Rochat et al., 1995, *J. Exper. Botany* 46:415–421.
Romeo et al., 1991, *Gene* 108:23–29.
Russel et al., 1993, *Plant Cell Rep.* 13:24–27.
Singletary et al., 1994, *Australian J. Plant Physiol.* 21:829–841.
Sivak and Preiss, 1995, *J. Environ. Poly. Degrad.* 3:145–152.
Smith–White and Preiss, 1992, *J. Mol. Evol.* 34:449–464.
Smith et al., 1989, *Plant Physiol.* 89:1279–1284.
Smith et al., 1997, *Ann. Rev. Plant Physiol. Plant Mol. Biol.* 48:67–87.
J. Sowokinos, 1976, *Plant Physiol.* 57:63–68.
Sowokinos and Preiss, 1982, *Plant Physiol.* 69:1459–1466.
Sowokinos et al., 1996, *Am. Potato J.* 73:386–387.
Spilatro and Preiss, 1987, *Plant Physiol.* 83:621–627.
Stark et al., 1992, *Science* 258:287–292.
Stark et al., 1993, *Front. Biomed. Biotechnol.* 1:30–38.
Stark et al., 1996, *Ann. NY Acad. of Sci.* 792:26–36.
Stitt et al., 1987, *Control of Photosynthetic Sucrose Formation*, Academic Press: San Diego 10:328–409.
Stitt et al., 1995, *Physiol. Plant Mol. Biol.* 46:341–367.
Sweetlove et al., 1995, *J. Exper. Botany* 46 (Suppl.):10.
Sweetlove et al., 1996, *Biochem. J.* 320:487–492.
Sweetlove et al., 1996, *Biochem. J.* 320:493–498.
Thomas et al., 1997, *Biochem. J.* 322:111–117.
Thomas et al., 1997, *Biochem. J.* 322:119–127.
Thorbjornsen et al., 1996, *Plant J.* 10:243–250.
Thorneycroft et al., 1996, *J. Exp. Botany* 47(Suppl.):35.
Twell et al., 1987, *Plant Mol. Biol.* 9:365–375.
Urbanowski et al., 1983, *J. Biol. Chem.* 258:2782–2784.
Vardy et al., 1996, *J. Ext. Botany* 47(Suppl.):78.
Visser et al., 1990, *J. Cell Biochem. Suppl.* 14E:271.
Witt et al., 1994, *J. Plant Physiol.* 143:625–631.
Witt et al., 1994, *Physiologia Plantarum* 92:9–16.
Chang and Stoltzfus, 1985, "Gene Expression from both Intronless and Intron–Containing Rous–Sarcoma Virus Clones is Specifically Inhibited by Anti–Sense RNA", Mol. Cell. Biol. 5:2341–2348.
De Graaff et al., 1988, "Isolation and Transformation of the Pyruvate Kinase Gene of *Aspergillus nidulans*", Curr. Genetics 13:315–321.
Hellinga and Evans, 1985, "Nucleotide Sequence and High–Level Expression of the Major *Escherichia coli* Phosphofructokinase", Eur. J. Biochem. 149:363–373.
Khursheed and Rogers, 1988, "Barley α–Amylase Genes", J. Biol. Chem. 263:18953–18960.
Sheehy et al., 1988, "Reduction of Polygalacturonase Activity in Tomato Fruit by Antisense RNA", Proc. Natl. Acad. Sci. USA 85:8805–8809.
Smith et al., 1988, "Antisense RNA Inhibition of Polygalacturonase Gene Expression in Transgenic Tomatoes", Nature 334:724–726.
von Schaewen et al., 1990, "Expression of a Yeast–Derived Invertase in the Cell Wall of Tobacco and Arabidopsis Plants Leads to Accumulation of Carbohydrate and Inhibition of Photosynthesis and Strongly Influences Growth and Phenotype Tobacco Plants", EMBO J. 9:3033–3044.
Yang et al., 1989, "Expression of a Synthetic Gene for Improved Protein Quality in Transformed Potato Plants", Plant Sci. 64:99–111.

METHOD FOR ALTERING CARBOHYDRATE METABOLITE LEVELS IN STORED POTATO TUBERS

This application is a division of copending Application Ser. No. 08/284,199 filed on Aug. 2, 1994, which is continuation of Application Ser. No. 07/991,451 filed on Dec. 16, 1992, now U.S. Pat. No. 5,387,756, which is a continuation of Application Ser. No. 07/628,216 filed on Dec. 17, 1990, now abandoned; the disclosures of all of which are incorporated herein by reference in their entirety.

FIELD OF THE INVENTION

The present invention relates to transgenic plants and their preparation.

BACKGROUND OF THE INVENTION

Phosphofructokinase (PFK; EC 2.7.1.11) is widely regarded as a key regulatory enzyme controlling the entry of carbon into glycolysis. Glycolysis, especially in plant cells, serves to supply both respiratory carbon for energy production and intermediates for other metabolic pathways. The potato tuber contains four forms of PFK (Kruger et al., Arch. Biochem. Biophys. 267:690–700) and pyrophosphate fructose-6-phosphate phosphotransferase (PFP; EC 2.7.1.90) which can catalyze the conversion of fructose-6-phosphate to fructose-6-bisphosphate. PFK is present in both the cytosol and the amyloplast while PFP is only known to occur in the cytosol.

BRIEF SUMMARY OF THE INVENTION

It has previously been thought that PFK alone controls the total glycolytic flux. However, we have now found that this is not the case. We introduced additional PFK into potato plants by genetic manipulation. Our results indicate that a substantial increase in PFK activity did not substantially alter flux through glycolysis but changed the pool sizes of intermediates. The results indicate that regulation of glycolytic flux may be achieved not only at the entry of carbon into the pathway but also exit from it. This finding has general applicability.

Accordingly, the present invention provides a process for the preparation of a transgenic plant, which method comprises:

(i) transforming a plant cell with a chimeric gene comprising (a) a suitable promoter and (b) a coding sequence the product of which causes modification of the amount of metabolic intermediate in glycolysis or in a pathway for the synthesis or degradation of starch, sucrose or reducing sugar; and (ii) regenerating a plant from the transformed cell.

The invention also provides the chimeric gene. A vector suitable for use in the present process comprises the chimeric gene such that the chimeric gene is capable of being expressed in a plant cell transformed with a vector. A plant cell according to the invention therefore harbors the chimeric gene such that the chimeric gene is capable of being expressed therein.

A transgenic plant can therefore be obtained which harbors in its cells the chimeric gene such that the chimeric gene is capable of being expressed in the cells of the plant. Seed or other propagules can be obtained from the transgenic plant and used to grow further plants stably transformed with the chimeric gene.

BRIEF DESCRIPTION OF THE DRAWINGS

In the accompanying drawings:

In FIG. 1 the broken lines indicate tentatively assumed pathways.

DETAILED DESCRIPTION OF THE INVENTION

Figure 1:
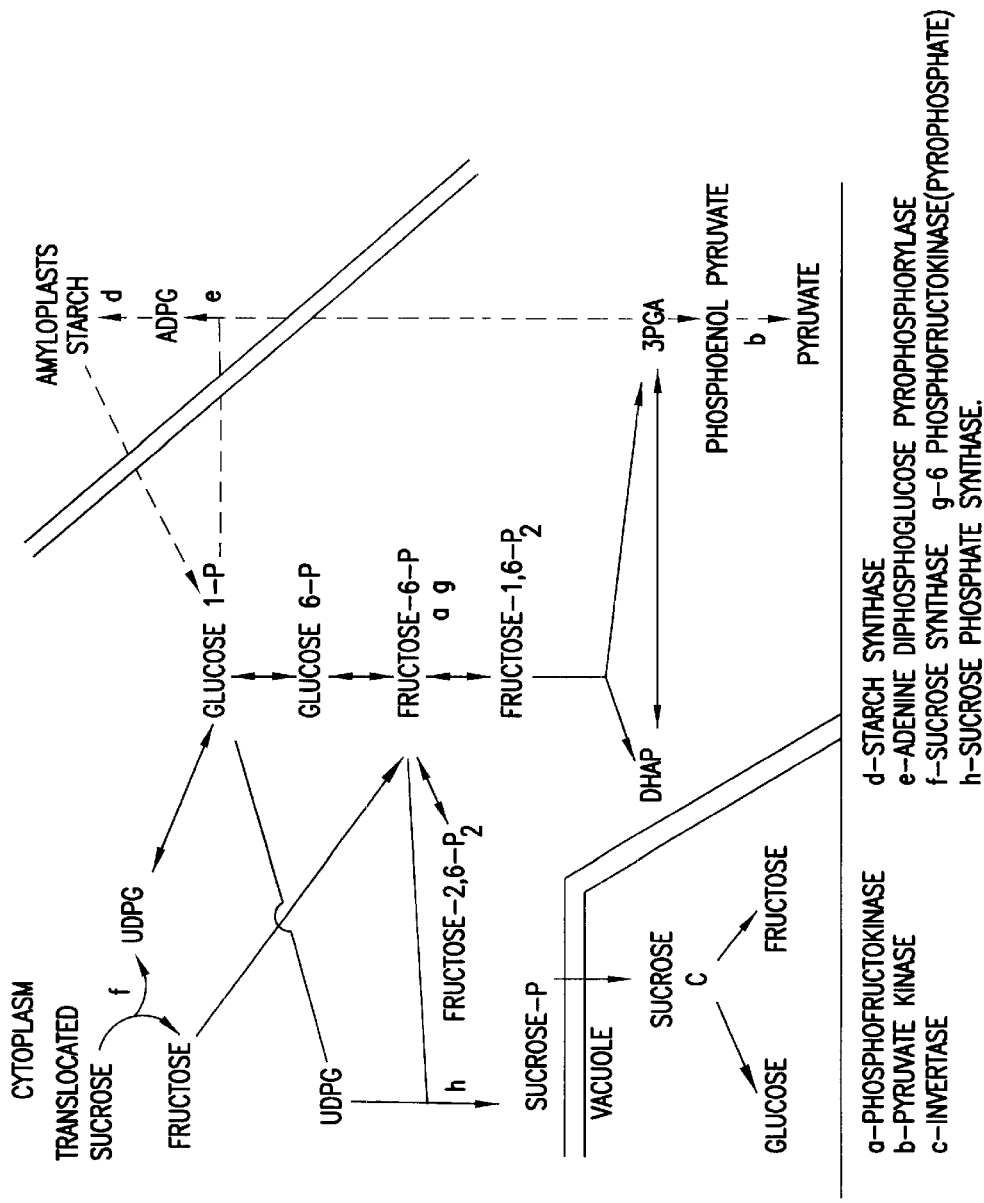
FIG. 1 shows a simplified diagram of carbohydrate metabolism with reference to plant storage tissues such, for example, as potato tubers.

The invention enables plant metabolism to be altered in a glycolytic pathway or in a pathway for the synthesis or degradation of starch, sucrose or a reducing sugar such as glucose or fructose. It enables the accumulation of pathway metabolites to be altered. Several applicable pathways are shown in FIG. 1 of the accompanying drawings. The invention is particularly applicable to potatoes. It had been expected that the introduction and expression of additional PFK in potato tuber cells would cause a high flux in the glycolytic pathway. Furthermore, if this gene had been introduced and expressed in the whole plant, it would not have been unreasonable to have expected that the plant would have died. In the event, though, it was surprising to find that after the introduction and expression of the PFK gene the plant did not die and the flux in the glycolysis metabolism pathway was not increased.

The storage of potato tubers in low temperature storage conditions normally results in less PFK activity. This, it is believed, leads to an increased production in the potato tubers of sucrose and reducing sugars. The accumulation of these sugars in the potato tubers presents a significant problem to processors of potatoes. For example, producers of crisps and chips (otherwise known respectively as potato chips and French fries) have found that the presence of an increased level of sugars tends to cause an undue browning of the products during the frying process.

When potato tubers of the subject invention are stored at low temperatures, the increased amount of PFK present therein ensures a continued flux into the glycolysis metabolism pathway. This in turn means that the flux level in the sucrose synthesis pathway is lower than has heretofore been the case with stored potato tubers. Thus significantly reduced levels of sucrose and reducing sugars accumulates in the stored tubers.

In the invention, a chimeric gene is constructed which comprises (a) a suitable promoter operably linked to (b) a coding sequence the product of which causes modification of the amount of a metabolic intermediate in glycolysis or in a pathway for the synthesis or degradation of starch, sucrose or reducing sugar. The chimeric gene may be constructed in any convenient fashion. The coding sequence is provided such that it is expressible in plant cells.

The promoter (a) should be capable of expressing the coding sequence of interest in a plant. The promoter may be a promoter capable of directing expression in a particular tissue of a plant and/or at particular stages of development. The promoter may be heterologous or homologous to the plant. A suitable promoter may be the 35S cauliflower mosaic virus promoter, a nopaline synthase or octopine synthase promoter, a patatin promoter or a small subunit ribulose bisphosphate carboxylase (RUBISCO) promoter. A promoter from tubers, e.g., patatin, is preferred for directing expression in potatoes, in particular potato tubers. A suitable promoter may be, for example, a constitutive promoter or a tissue-specific promoter.

The coding sequence (b) can encode an enzyme which regulates the amount of a metabolic intermediate of a specific pathway. The pathway may be the glycolytic pathway. Glycolysis is the sequence of reactions which converts glucose to pyruvate with concomitant production of ATP or NADH and is also termed the Embden-Meyerhof-Parnas pathway.

Sucrose consists of glucose and fructose coupled via an alpha 1–2 O-glycosidic bond. Pathways of sucrose synthesis therefore involve enzyme steps that produce suitable intermediates to form this linkage. Starch is a polymer which consists mainly of alpha 1–4 linked glucose with varying amounts of 1–6 linked glucose. Thus pathways of starch synthesis involve steps that produce suitable intermediates to form this polymer.

A coding sequence is selected which when expressed in plant cells will increase or decrease the metabolism of a pathway mentioned above. The coding sequence (b) may encode for a pathway enzyme or an active modified form of a pathway enzyme, for example a truncated pathway enzyme. The pathway enzyme may be, for example, PFK (EC 2.7.1.11), pyruvate kinase (PK; EC 2.7.1.40), acid invertase (EC 3.2.1.26), starch synthase (EC 2.4.1.21), adenosine diphosphoglucose pyrophosphorylase (ADPGPP; EC 2.7.7.27), sucrose synthase (EC 2.4.1.13), 6-phosphofructokinase (pyrophosphate) (EC 2.7.1.90) or sucrose phosphate synthetase (SPS; EC 2.4.1.14).

The coding sequence may be from a plant gene or a non-plant gene such as a microbial gene. It may be from a bacterial gene, for example a gene from *E. coli*, or from yeast, for example *Saccharomyces cerevisiae*. In particular, a PFK coding sequence may be provided by the pfkA gene from *E. coli* or by a pfk gene from *Solanum tuberosum*. An acid invertase coding sequence may be provided from *Saccharomyces cerevisiae*.

Plant cells can be transformed with the chimeric gene by direct DNA uptake, typically by way of a DNA fragment comprising the chimeric gene. Alternatively, there may be used a vector incorporating the chimeric gene. The chimeric gene typically includes transcriptional control sequences, for example a promoter as above, and translational initiation and/or termination sequences. Plant terminator and polyadenylation sequences may be present. A vector typically contains a region which enables the chimeric gene to be transferred to and stably integrated in the plant cell genome.

The vector is therefore typically provided with transcriptional regulatory sequences and/or, if not present at the 3'-end of the coding sequence of the gene, a stop codon. A DNA fragment may therefore also incorporate a terminator sequence and other sequences which are capable of enabling the gene to be expressed in plant cells. An enhancer or other element able to increase or decrease levels of expression obtained in particular parts of a plant or under certain conditions, may be provided in the DNA fragment and/or vector. The vector is also typically provided with an antibiotic resistance gene which confers resistance on transformed plant cells, allowing transformed cells, tissues and plants to be selected by growth on appropriate media containing the antibiotic.

Transformed plant cells can be selected by growth in an appropriate medium. Plant tissue can therefore be obtained comprising a plant cell which harbors a gene encoding an enzyme under the control of a promoter, for example in the plant cell genome. The gene is therefore expressible in the plant cell. Plants can then be regenerated which include the gene and the promoter in their cells, for example integrated in the plant cell genome such that the gene can be expressed. The regenerated plants can be reproduced and, for example, seed obtained.

A preferred way of transforming a plant cell is to use *Agrobacterium tumefaciens* containing a vector comprising a chimeric gene as above. A hybrid plasmid vector may therefore be employed which comprises:

(a) a chimeric gene containing regulatory elements capable of enabling the gene to be expressed when integrated in the genome of a plant cell;

(b) at least one DNA sequence which delineates the DNA to be integrated into the plant genome; and (c) a DNA sequence which enables this DNA to be transferred to the plant genome.

Typically the DNA to be integrated into the plant cell genome is delineated by the T-DNA border sequences of a Ti-plasmid. If only one border sequence is present, it is preferably the right border sequence. The DNA sequence which enables the DNA to be transferred to the plant cell genome is generally the virulence (vir) region of a Ti-plasmid.

The gene coding for the enzyme and its transcriptional and translational control elements can therefore be provided between the T-DNA borders of a Ti-plasmid. The plasmid may be a disarmed Ti-plasmid from which the genes for tumorigenicity have been deleted. The gene and its transcriptional control elements can, however, be provided between T-DNA borders in a binary vector in trans with a Ti-plasmid with a vir region. Such a binary vector therefore comprises:

(a) the chimeric gene under the control of regulatory elements capable of enabling the gene to be expressed when integrated in the genome of a plant cell; and (b) at least one DNA sequence which delineates the DNA to be integrated into the plant genome.

*Agrobacterium tumefaciens*, therefore, containing a hybrid plasmid vector or a binary vector in trans with a Ti-plasmid possessing a vir region can be used to transform plant cells. Tissue explants such as stems or leaf discs may be inoculated with the bacterium. Alternatively, the bacterium may be co-cultured with regenerating plant protoplasts. Plant protoplasts may also be transformed by direct introduction of DNA fragments which encode the enzyme and in which the appropriate transcriptional and translational control elements are present or by a vector incorporating such a fragment. Direct introduction may be achieved using electroporation, polyethylene glycol, microinjection or particle bombardment.

Plant cells from angiospermous, gymnospermous, monocotyledonous or dicotyledonous plants can be transformed according to the present invention. Monocotyledonous species include barley, wheat, maize and rice. Dicotyledonous species include cotton, lettuce, melon, pea, petunia, potato, rape, soybean, sugar beet, sunflower, tobacco and tomato. Potato cultivars to which the invention is applicable include Desiree, Maris Bard, Record and Russet Burbank.

Tissue cultures of transformed plant cells are propagated to regenerate differentiated transformed whole plants. The transformed plant cells may be cultured on a suitable medium, preferably a selectable growth medium. Plants may be regenerated from the resulting callus. Transgenic plants are thereby obtained whose cells incorporate the chimeric gene in their genome, the chimeric gene being expressible in the cells of the plants. Seed or other propagules from the regenerated plants can be collected for future use.

A preferred procedure in respect of the potato variety Record is as follows.

Plant Material

Record shoot cultures are maintained in vitro on Murashige and Skoog (MS) medium in Magenta GA-7 containers at 22° C. (16h/8h light/dark). These are nodally sub-cultured every 3 weeks. In vitro shoots of 2–3 inches (5–7.5 cm) height are potted in 2.5 inches (6.4 cm) pots of Levingtons F1 compost. They are weaned in a propagator for one week in a growth room at 18° C. (16h/8h light/dark). The propagator is removed and the plants repotted at 3 weeks into 5 inch (12.7 cm) pots. At 5–7 weeks the plants are used for transformation.

*Agrobacterium tumefaciens*

Liquid overnight cultures of suitable strains e.g., LBA4404, C58#3 are grown at 28° C. to an $OD_{600}$ of 0.8 in L-broth (see Media, below).

Cocultivation

The youngest four most expanded leaves are taken and surface sterilized in 10% Domestos™ (commercial bleach) for 15 minutes. Leaves are rinsed thoroughly with sterile water and then cut into discs with a 7 mm cork borer. The discs are mixed with the Agrobacterium for 1–5 minutes, blotted dry on filter paper (Whatman No. 1) and then placed on callusing medium (see Media, below) in 90 mm triple vented petri dishes, lower epidermis down. The 90 mm triple vented petri dishes are sealed with tape, cut to allow gas exchange and then incubated at 22° C. (16h/8h light/dark). The discs are transferred to callusing medium plus 500 μg $ml^{-1}$ of claforan and 30 μg $ml^{-1}$ kanamycin after 48 hours. This removes bacteria and selects for transformed cells.

Regeneration of Transformed Shoots

After 1 week, the discs are transferred to shooting medium (see Media, below) containing the same antibiotics. Further transfers are made onto the same medium until shoots can be excised (usually about 4 weeks). Shoots with calli are transferred to MS medium with cefotaxime in well ventilated containers, e.g., Magenta. Transformants are maintained, after several passages with cefotaxime to remove bacteria, on MS medium. They may be removed from in vitro, weaned and grown to maturity as described for the stock plants.

The process yields transformed Record plants at a frequency of up to 30% of the discs cocultivated.

| Media | |
|---|---|
| L-broth | 10 g $l^{-1}$ bactotryptone |
| | 5 g $l^{-1}$ yeast extract |
| | 5 g $l^{-1}$ sodium chloride |
| | 1 g $l^{-1}$ glucose |
| Callusing medium | MS with 3% sucrose |
| | 0.5 mg $l^{-1}$ 2,4-D |
| | 2.5 mg $l^{-1}$ BAP |
| Shooting medium | MS plus 3% sucrose |
| | 2.5 mg $l^{-1}$ BAP |
| | 1.0 mg $l^{-1}$ $GA_3$ |

EXAMPLES

The following examples illustrate the invention.

Example 1

Production of PFK in Potato Tubers

Figure 2:
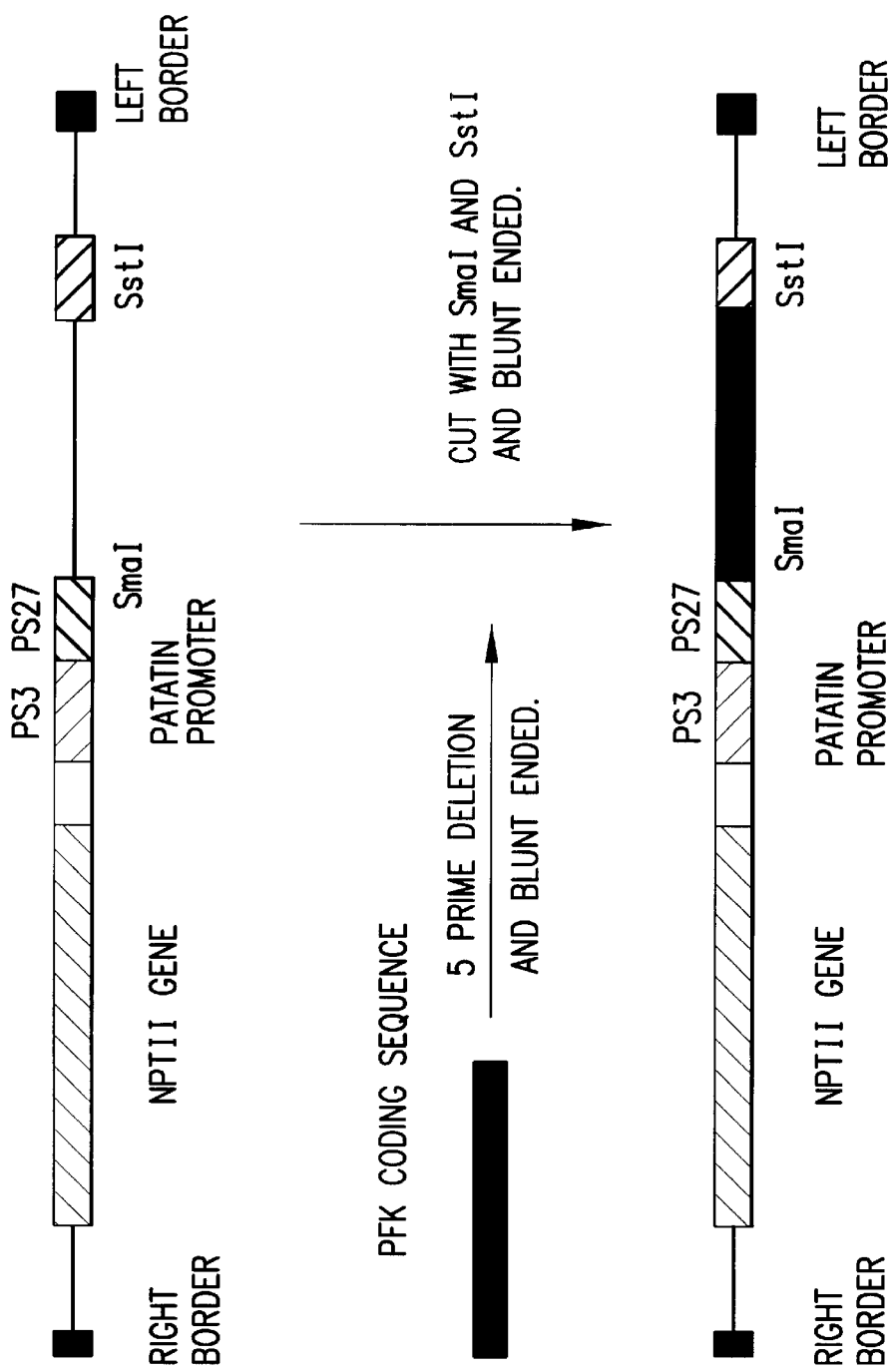
FIG. 2 shows the procedure used to produce a chimeric PFK gene.

The procedure used to produce a chimeric PFK gene to provide tuber-specific expression of PFK is illustrated in FIG. 2. The PFK coding sequence was obtained from a clone of the pfka gene as described by Hellinga H. W. and Evans P. R., 1985, Eur. J. Biochem. 149:363–373. The PFK coding sequence was isolated so that only 20 basepairs remained before the translational start site. More specifically the *E. coli* pfkA gene on plasmid pHE1012 was deleted at the 5'-end to 20 bp from the translational start site and 50 bp from the 3'-end of the coding sequence. This was then blunt end ligated into the plasmid pFW4101 in place of the GUS (β-glucuronidase) coding sequence to give plasmid pFW4023. pFW4101 was constructed with a patatin promoter made from two genomic clones PS3 and PS27. The patatin fragments PS3 and PS27 were derived from the genomic clones described by Mignery et al. 1988, Gene 62:27–44. The fragments consist of −3.5 kb to −1 kb of PS3 and −1 kb to +3 kb of PS27 numbered in relation to the translation start.

*E. coli* harboring pFW4023 and *E. coli* harboring pFW4101 were deposited at the National Collection of Industrial and Marine Bacteria, Aberdeen, GB on Jul. 5, 1990 under accession numbers NCIMB 40305 and NCIMB 40306.

The vectors pFW4101 and pFW4023 were transferred separately into *Agrobacterium tumefaciens* strain LBA 4404 by triparental mating. The Agrobacterium strains were used to transform the potato cultivar Desiree. A large family of over 60 transgenic plants were produced. Southern analysis showed that the plants contained between one and eight copies of the *E. coli* pfkA gene. Some of these plants produced tubers which contained considerable PFK activity. PFK activity was measured as described by Kruger et al. 1989, Arch. Biochem. Biophys. 267:690–700. Intermediates were extracted with ice cold perchlorate and measured enzymatically. The results are shown in Table 1.

TABLE 1

PFK Activity and amount of glycolytic intermediates

|  | PFK transgenic | | GUS transgenic | | | |
|---|---|---|---|---|---|---|
|  | mean | (SD) | mean | (SD) | t value | P |
| PFK activity[1] | 625 | (206) | 29 | (12) | 4.07 | >99 |
| Glc-6P[2] | 78 | (8.9) | 100 | (21) | 1.97 | >95 |
| Fru-6P[2] | 21 | (4.2) | 29 | (9) | 1.77 | >90 |
| Ratio | 3.7 | (0.56) | 3.7 | (0.66) | 0.9 | N.S. |
| PEP[2] | 82 | (20.4) | 28 | (8.0) | 3.54 | >99 |
| Pyr[2] | 44 | (22.6) | 37 | (16) | 0.80 | N.S. |
| Ratio | 2.5 | (1.3) | 1.0 | (0.6) | 2.20 | >95 |

[1]PFK activity is given as nmoles $min^{-1}$ $g^{-1}$ (fr. wt.)
[2]Intermediates are given as nmoles $g^{-1}$ (fr. wt.)

Figure 3:
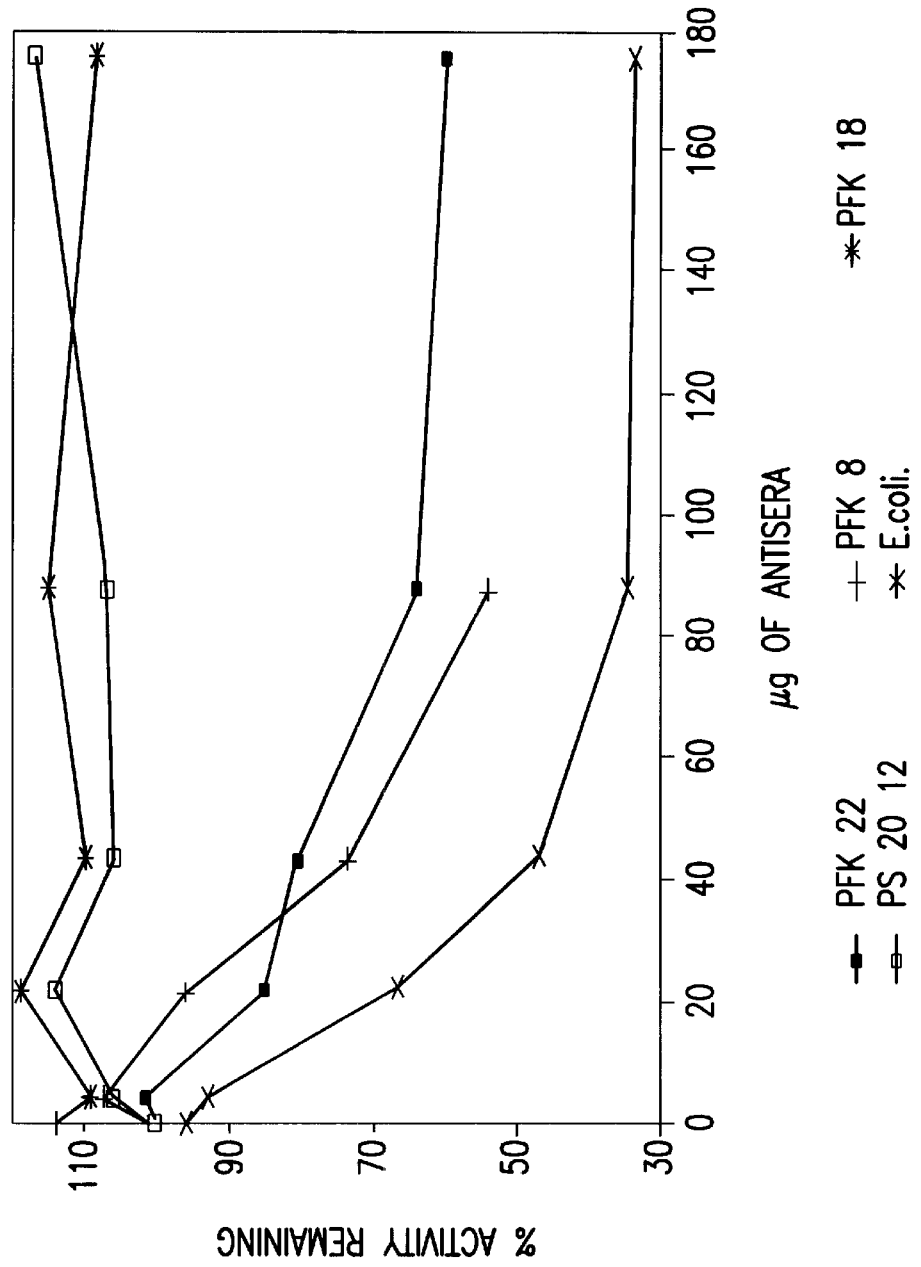
FIG. 3 shows the inmunodetection of $E.$ $coli$ PFK activity. PFK was immunoactivated with antisera raised to the introduced $E.$ $coli$ PFK. Antisera was mixed with equal amounts of PFK activity (1 nmole F6P consumed $min^{-1}$) from two transgenic lines expressing PFK (PFK22, ■; PFK8, +), two transgenic lines one not expressing PFK (PFK16, *) and expressing GUS (PS20-12, □), or $E.$ $coli$ PFK (x). Bound PFK was removed with protein A and the activity not removed assayed (Kruger et al., 1989, Arch. Biochem. Biophys. 267:690–700).

Assays containing mixtures of extracts from two plants differing in amount of activity did not reveal the presence of activators or inhibitors (data not shown). Two lines of evidence were sought to demonstrate that the observed increase in PFK activity was due to E. coli PFK. Firstly, antisera raised to this enzyme was used to immunoinactivate specifically the E. coli PFK activity in crude protein extracts from tubers. The results are shown in FIG. 3. A considerable proportion of the activity could be removed in lines showing increased activity but not in lines expressing GUS or not showing elevated activity (FIG. 3). Mixtures of line 12 (GUS) control plants with either E. coli PFK or line 22 (elevated PFK) gave the expected results indicating that the immunoinactivation was not due to inhibitors in the control plants. Secondly, the antisera was used with Western blots to show clearly the appearance of the 36 kD E. coli PFK polypeptide of the correct molecular weight. This band does not coincide with any predominant potato protein or potato PFK which has subunit molecular weights between 55 and 63 kD.

To discover whether this increase in enzyme activity, which in the strongest expressing tissue was 40 fold, had altered glycolytic flux we initially measured the rate of respiration by Warburg manometry. Respiratory rates were determined by Warburg manometry (Umbreit). Tubers were bathed in 2.7 ml of 20 mM phosphate buffer pH 5.2 containing 0.5 mM glucose. $CO_2$ was absorbed in 10% KOH. These results are shown in Table 2.

TABLE 2

Respiration in Tubers
Gas exchange nmol $min^{-1}g^{-1}$ fr. wt. (S.D.)

|  | PFK Transgenic | GUS Transgenic |
|---|---|---|
| Oxygen Uptake | | |
| at 2 h | 29.4 (8.9) | 36.3 (7.2) |
| at 5 h | 49.8 (4.1) | 55.2 (10.4) |

TABLE 2-continued

Respiration in Tubers
Gas exchange nmol $min^{-1}g^{-1}$ fr. wt. (S.D.)

|  | PFK Transgenic | GUS Transgenic |
|---|---|---|
| $CO_2$ Release | | |
| at 2 h | 22.2 (3.2) | 24.3 (8.6) |
| at 5 h | 33.7 (7.7) | 44.0 (9.0) |

There was no indication of a change in oxygen uptake or carbon dioxide evolution. Thus if respiration determined by gas exchange is an indication of glycolytic flux, excess PFK has not altered it. However in these tubers it is possible that a substantial amount of the respired carbohydrate entered the citric acid cycle via the pentose phosphate pathway and not glycolysis. Both pathways consume glucose-6-P. If this were the case then the addition of a large excess of PFK might change the distribution of metabolism but not the overall flux.

We therefore determined the rate of release of $^{14}CO_2$ from $6^{14}C$-glucose and from $1-^{4}C$-glucose. The ratio of release 6C/1C indicates the contribution of glycolysis to respiration. In both PFK and GUS transgenic plants the ratio was approximately 0.2 after 40 min. of incubation in $^{14}C$-glucose, 0.3 after 2 h and 0.4 after 4 h. Thus the presence of up to 40 fold excess of PFK activity has not altered the relative contributions of glycolysis and pentose phosphate pathway to glycolytic flux.

These results suggest that PFK is not regulating the entry of carbon into glycolysis in potato tubers. We therefore measured the amounts of glucose-6-P, and fructose-6-P, phosphoenol pyruvate (PEP) and pyruvate (Table 1). Elevated PFK activity has clearly lowered the amount of hexose-phosphate present but the mass action ratio (Glc-6P:Fru-6P) has remained the same and is approximately 4. This is near the equilibrium constant of glucose-6-phosphate isomerase (Sicher and Kremer, 1990, Pl. Science 67:47–56). More notable however is the large increase in PEP and change in the ratio of PEP:pyruvate. This strongly suggests that the increased level of PFK has led to more carbon entering glycolysis for a given respiratory flux and in those plants where PFK activity is increased the enzymes (probably pyruvate kinase and PEP carboxylase) that use PEP are strongly influencing the flux.

Plants of cv Desiree transformed as described above were grown in the field and the amount of sucrose in the potato tubers measured at harvest was less in lines expressing high PFK. The difference between sucrose content is significant at P=0.05. Thus this modification of glycolysis can cause an alteration in a pool of metabolite in a related pathway of carbohydrate metabolism (as illustrated in FIG. 1).

TABLE 3

Alteration in sucrose content of tubers

| Line | PFK Activity nmol $min^{-1}$ $g^{-1}$ (fr. wt.) | Sucrose content % w/w |
|---|---|---|
| PFK22 | 1011 | 0.219 |
| PFK36 | 379 | 0.293 |

TABLE 3-continued

Alteration in sucrose content of tubers

| Line | PFK Activity nmol min$^{-1}$ g$^{-1}$ (fr. wt.) | Sucrose content % w/w |
|---|---|---|
| PS20-24 | 18 | 0.347 |
| PS20-6 | 18 | 0.358 |

Such alterations are not confined to potato tubers. The patatin promoter can be induced to express in leaf tissue by incubating them in a medium of sucrose (Rocha-Sosa et al., 1989, EMBO J. 8:23–29). Discs were cut from leaves of plants (line PFK22) containing the chimeric PFK gene and control plants containing the chimeric GUS gene (line PS20–12). After incubation in the light on a medium containing 1% sucrose, to cause the expression of the PFK gene, the tissues were analyzed for changes in intermediates.

The results in Table 4 show that in a tissue other than a tuber the alterations in the activity of PFK can alter metabolic intermediates.

TABLE 4

Ratio of $\dfrac{\text{Amount of intermediate in line PFK-22}}{\text{Amount of intermediate in line PS20-12}}$ (S.D.)

| Fru-2,6-P$_2$ | PEP | Pyruvate |
|---|---|---|
| 2.23 (±0.37) | 1.18 (±0.3) | 0.49 (±0.1) |

Example 2

Expression of *E. coli* PFK in Rice Callus

A chimeric gene was constructed as described in FIG. 2 but a 35S promoter replaced the patatin promoter.

This gene was used to transform rice protoplasts and the callus assayed for PFK activity. Control callus tissue had activities of up to 1500 nmol min$^{-1}$ g$^{-1}$ (fr. wt.) The transformed callus had activities of 3000 nmol min$^{-1}$ g$^{-1}$ (fr. wt.) Thus, it is possible to express this chimeric gene in monocotyledonous plants such as rice.

What is claimed is:

1. A method for reducing the level of sucrose or a reducing sugar in a potato tuber stored at low temperature, comprising:
    a) obtaining a potato tuber from a transgenic potato plant, which transgenic potato plant contains a chimeric gene construct comprising a promoter operably linked to a coding sequence for a phosphofructose kinase (E.C. 2.7.1.11), which promoter directs expression of the coding sequence in the potato tuber; and
    b) storing the potato tuber at low temperature, thereby reducing the level of sucrose or the reducing sugar.

2. A method for prolonging the dormancy of a stored potato tuber, comprising:
    a) obtaining a potato tuber from a transgenic potato plant, which transgenic potato plant contains a chimeric gene construct comprising a promoter operably linked to a coding sequence for a phosphofructose kinase (E.C. 2.7.1.11), which promoter directs expression of the coding sequence in the potato tuber; and
    b) storing the potato tuber, thereby inhibiting sprouting during storage of the stored potato tuber.

* * * * *